United States Patent [19]
Gröschl et al.

[11] Patent Number: 5,976,324
[45] Date of Patent: Nov. 2, 1999

[54] REMOVAL OF WATER FROM REACTION MIXTURES

[75] Inventors: Andreas Gröschl; Adolf Winkler; Josef Bremen, all of Leverkusen, Germany

[73] Assignee: Bayer Aktiengesellschaft, Leverkusen, Germany

[21] Appl. No.: 08/946,482

[22] Filed: Oct. 7, 1997

[30] Foreign Application Priority Data

Oct. 14, 1996 [DE] Germany ............ 196 42 326
Nov. 8, 1996 [DE] Germany ............ 196 46 113

[51] Int. Cl.⁶ ............ B01D 3/00; B01D 15/00; C07C 27/26; C07C 67/08
[52] U.S. Cl. ............ 203/14; 159/DIG. 27; 203/15; 203/18; 203/29; 203/39; 203/86; 210/500.26; 210/500.27; 210/500.31; 210/500.32; 210/500.38; 210/500.39; 210/500.41; 210/640; 568/916
[58] Field of Search ............ 203/14, 53.55, 203/86, 91, 18, 15, 29, 39, DIG. 13; 159/DIG. 28, DIG. 27; 210/638, 640, 500.27, 500.31, 500.32, 500.38, 500.39, 500.41, 500.26; 568/913, 916, 851; 558/277; 560/1; 554/170; 435/134

[56] References Cited

U.S. PATENT DOCUMENTS

| | | | |
|---|---|---|---|
| 4,876,403 | 10/1989 | Cohen et al. ............ | 568/913 |
| 4,895,989 | 1/1990 | Sander et al. ............ | 568/851 |
| 4,900,402 | 2/1990 | Kaschemekat et al. ............ | 203/19 |
| 5,009,783 | 4/1991 | Bartels ............ | 210/500.41 |
| 5,156,740 | 10/1992 | Brüschke ............ | 210/490 |
| 5,248,427 | 9/1993 | Spiske et al. ............ | 210/640 |
| 5,288,818 | 2/1994 | Livingston, Jr. et al. ............ | 210/640 |
| 5,334,314 | 8/1994 | Neel et al. . | |
| 5,360,923 | 11/1994 | Nickel et al. ............ | 558/277 |
| 5,427,687 | 6/1995 | Blum et al. ............ | 210/638 |
| 5,648,517 | 7/1997 | Müller et al. ............ | 560/205 |

FOREIGN PATENT DOCUMENTS

| | | | |
|---|---|---|---|
| 0294827 | 12/1988 | European Pat. Off. ............ | B01D 13/00 |
| 0299577 | 1/1989 | European Pat. Off. ............ | C07C 29/70 |
| 0476370 | 3/1992 | European Pat. Off. ............ | C07C 67/52 |
| 0498509 | 8/1992 | European Pat. Off. . | |
| 0506159 | 9/1992 | European Pat. Off. . | |
| 0592883 | 4/1994 | European Pat. Off. ............ | B01D 61/36 |
| 0691324 | 1/1996 | European Pat. Off. ............ | C07C 67/08 |
| 3610011 | 1/1989 | Germany ............ | B01D 17/00 |
| 4019170 | 12/1991 | Germany ............ | B01D 53/22 |
| 61-64305 | 4/1986 | Japan . | |
| 1107805 | 4/1987 | Japan . | |
| 09299764 | 11/1997 | Japan . | |
| 2271992 | 5/1994 | United Kingdom . | |

OTHER PUBLICATIONS

F.P. Helmus, Dampfpermeation Trennvrmögen, Prozess entwicklung and Einsatzmöglichkeiten, pp. 1–11 and 140–143, (Feb. 17, 1994).

S. Klatt, Zum Einsatz der Pervaporation im Umfeld der chemischen Industrie, pp. 1–125. (Apr. 30, 1993).

R. Gref, et al., Coupling Between Pervaporation and Chemical Reactions; Esterification of Carboxylic Acids Aided by Pervaporation, pp. 344–371, (1989).

H. Kita, et al., The Esterification of Oleic Acid with Ethanol Accompanied by Membrane Separation, Chemistry Letters, pp. 2053–2056, (1987).

R. Rautenbach, et al., Membranverfahren zur Fraktionierung von Gemischen mit organischen Komponenten*, Chem.–Ing.–Tech., 61, No. 7, pp. 535–544, (1989).

*Primary Examiner*—Virginia Manoharan
*Attorney, Agent, or Firm*—Joseph C. Gil; Diderico van Eyl

[57] ABSTRACT

A process as been found for the removal of water from reaction mixtures of acids or acid anhydrides or of aqueous alkali metal hydroxide solutions with alcohols using vapor permeation/pervaporation at the boiling point of the reaction mixture, which includes initially introducing the lowest-boiling educt in less than the stoichiometric amount, based on the other particular educt, together with this other educt, heating the reaction mixture to the boiling point and freeing the vapor mixture, which is formed from the boiling reaction mixture and includes chiefly water and the lowest-boiling component, from water on a membrane, recycling the vapor mixture which has been freed from water into the reaction mixture and topping up the reaction mixture with the lowest-boiling educt in the course of the reaction.

16 Claims, No Drawings

REMOVAL OF WATER FROM REACTION MIXTURES

BACKGROUND OF THE INVENTION

1. Field of the Invention

The present invention relates to a process for the removal of water from reaction mixtures for the esterification of acids or acid anhydrides with alcohols or for the preparation of alcoholates from aqueous alkali metal hydroxide solutions and alcohols at the boiling point of the reaction mixture, in which the lowest-boiling educt is first employed in less than the stoichiometric amount, the resulting vapor mixture of chiefly water and the lowest-boiling component is freed from water on a membrane, the vapor mixture which has been freed from water is recycled into the reaction mixture and the reaction mixture is topped up with the lowest-boiling educt in the course of the reaction.

2. Description of the Related Art

In chemical equilibrium reactions in which water is formed, it is already known to remove this by pervaporation or vapor permeation with the aid of semipermeable membranes and as a result to shift the equilibrium and thus to bring the reaction to completion. Such membrane processes for fraction of mixtures with organic components are described in detail in the literature (Rautenbach, Chem. Ing. Techn. 61 (1989) pages 539–544). Pervaporation and vapor permeation have also already been described in detail (DE 3 610 011, DE-A 4 019 170 and EP-A 294 827).

Generally, in these processes, the substance mixture to be separated (feed) is fed along a membrane which has different permeabilities to the individual compounds of the approaching substance mixture. The driving force for transportation of matter through the membrane here is a transmembrane difference in the electrochemical potential of the individual substances of the feed mixture. In the case of pervaporation and vapor permeation, this potential difference is accentuated by a vacuum applied to the membrane side facing away from the feed (permeate side) or by flushing the permeate side with inert gas, which has the result of diverting the preferentially permeating components out of the feed. An increased pressure is in general applied to the feed side of the membrane. The depleted feed is called the retained material and the substance amounts passing to the permeate side are called the permeate. The separation properties of membranes are highly temperature-dependent, but are limited by the heat stability of the membrane employed. As, for example, the heat stability of the membrane Pervap 1000 from Deutsche Carbone, GFT, of the polyvinyl alcohol/polyacrylonitrile type is stated as 100° C.

Pervaporation is described, inter alia, by Klatt (dissertation paper "On the use of Pervaporation in the Environment of the Chemical Industry", Rheinisch-Westfälische Technische Hochschule (RWTH) Aachen 1993). Pervaporation is distinguished by the fact that the feed mixture is fed in liquid form just below the boiling point at the given system pressure. The system pressure must be chosen such that, at the membrane, the temperature of the substance mixture to be separated corresponds as far as possible to the optimum temperature in respect of permeate flow and selectivity, but must in no way be above the maximum permitted operating temperature of the membrane (membrane stability). Vapor permeation is described in detail, inter alia, by Helmus (dissertation paper "Vapor permeation-separation capacity, process development and possible uses", RWTH Aachen 1994). In vapor permeation, in contrast to pervaporation, the feed is fed over the membrane in vapor form.

Kitha reports in Chemistry Letters (Chem. Soc. of Japan) 1987 2053–2056 on the esterification of carboxylic acids with alcohols, for example with ethanol, in which ethanol/water corresponding to the thermodynamic equilibrium is evaporated off from the reaction mixture initially introduced, the escaping vapor is fed along a vapor permeation membrane, and the retained material depleted of water is recycled into the reaction mixture. The degrees of conversion which can be achieved are increased up to complete conversion of the carboxylic acid with the process described. The membranes employed are polyimide, chitosan and Nafion membranes, the polyimide membranes employed having adequate selectivities in particular. Gref (Proc. Fourth Int. Conf. Pervaporation, Proc. Chem. Ind. 1989, 344) also describes the use of pervaporation for removing water of reaction from the circulation in the preparation of carboxylic acid esters using PVA membranes. Sander (EP 299 577) describes the use of a PVA membrane for selective removal of water from the vapor of a reaction mixture during the preparation of alcoholates from NaOH and alcohol. Blum (De 4 019 170 A1) reports on the successful use of vapor permeation for removal of water in the preparation of dodecyl acetate and isopropyl myristate (esterification reactions of alcohols with carboxylic acid) in a bubble reactor. EP 0 476 370 describes the use of pervaporation/vapor permeation for removal of water from a mixture comprising water and alcohols and/or carboxylic acids and/or carboxylic acid esters, a membrane which has been obtained by plasma polymerisation being used. EP-A 691 324 describes the use of vapor permeation for the preparation of maleic acid alkyl esters from maleic anhydride and alcohol, the vapor mixture fed to the module comprising condensed contents in order to avoid overheating of the vapor mixture when flowing over the membrane and the associated reduction in the performance of the membrane.

All the procedures described have the common feature that the lowest-boiling educt (in many cases the alcohol) is added at least stoichiometrically, but as a rule in more than the stoichiometric amount. It is attempted by this means to shift the reaction equilibrium to higher degrees of conversion of the acid employed or the alkali metal hydroxide employed, so that the reaction time is simultaneously shortened in this way. Kitha (see above) employs a stoichiometric excess of ethanol of 2:1 and 3:1 in his studies on the esterification of oleic acid with ethanol. Sander (see above) mentions an alcohol excess of 1:2 to 1:10 for the preparation of alcoholates from alkali metal hydroxide and alcohol with removal of the water of reaction from the circulation by vapor permeation (page 2 column 2 line 20). Gref (see above) has systematically investigated the influence of the excess factor in the esterification of propionic acid with isopropanol when pervaporation is employed to remove the water of reaction from the circulation, and comes to the conclusion that a reduction in the excess factor of an educt leads to longer reaction times in respect of the conversion of the minor component (FIG. 13 there). Gref states the stoichiometric use of the educt as the optimum. Blum (see above) also indicates an optimum with stoichiometric use of the educts and use of vapor permeation for removal of the water of reaction from the circulation.

SUMMARY OF THE INVENTION

Surprisingly, it has now been found that the reaction times in esterification reactions and in the formation of alkali metal alcoholates from aqueous alkali metal hydroxide solutions and alcohols using vapor permeation or pervaporation can be reduced significantly if the lowest-boiling educt (in many cases the alcohol) is initially introduced in less than the stoichiometric amount, together with the other particular educt, at the start of the reaction, the reaction mixture is brought to the boiling point, if appropriate in the presence of a catalyst in the case of an esterification reaction, the vapor mixture which is formed from the boiling reaction mixture and escapes is passed as the feed along a membrane, on which water is diverted out, the vapor mixture freed from water in this way (retained material) is recycled into the reaction mixture, and in the course of the reaction the mixture is topped up, for complete reaction, with the educt, which has been initially introduced in less than the stoichiometric amount.

The invention accordingly relates to a process for the removal of water from reaction mixtures of acids or acid anhydrides or of aqueous alkali metal hydroxide solutions with alcohols using vapor permeation/pervaporation at the boiling point of the reaction mixture, which comprises initially introducing, as the reaction mixture, the lowest-boiling educt, together with the other particular educt and, in the case of esterifications, with or without an esterification catalyst, the lowest-boiling educt being employed in less than the stoichiometric amount, based on the other particular educt, heating the reaction mixture to the boiling point and feeding the vapor mixture formed from the boiling reaction mixture, if appropriate together with contents of a condensed phase formed from the vapor mixture, as a feed along a membrane on which water is removed, recycling the vapor mixture depleted in water into the reaction mixture and topping up the reaction mixture with the lowest-boiling educt during the reaction.

DETAILED DESCRIPTION OF THE INVENTION

The process according to the invention, both in the case of esterification and in the case of alcoholate formation, has the characteristic common features that two educts—in the case of esterification an acid or an acid anhydride and an alcohol, and in the case of alcoholate formation an aqueous alkaline earth metal hydroxide solution and an alcohol—are reacted with one another with the emergence of water, these reactions proceed in the presence of water in the reverse direction with re-formation of the educts (instead of the educt acid anhydride, however, the corresponding acid is re-formed) and are thus an equilibrium reaction, and that finally, by diverting the water out of the reaction mixture, the reaction progresses and comes to completion with consumption of the educts.

The water to be diverted out according to the invention is primarily the water of reaction, for example from the equations:

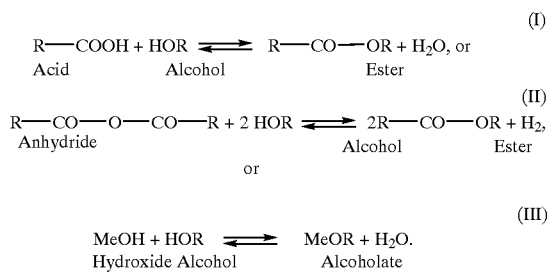

Inorganic acids are of course also possible acids, and cyclic anhydrides are of course also possible anhydrides.

The phenols are equivalent to the alcohols as the organic hydroxy compound in the esterification and are expressly included according to the invention.

In addition to the water of reaction, however, water of another origin can also be diverted out of the reaction mixture in the process according to the invention. Such water is, for example, dilution water of the alkali metal hydroxide solution educt, or that of the acid or alcohol educts in diluted form, thus, for example, the use of azeotropically boiling 96% strength ethanol or other educt/water azeotropes in which prior separate removal of water can be omitted, and, finally, water of crystallization, for example in the case of oxalic acid $(COOH)_2.2H_2O$. Such water and water of further origin still is known to the expert.

Alcohol components which can be employed in the process according to the invention are straight-chain or branched, open-chain or cyclic, saturated or unsaturated $C_1$–$C_8$-alcohols, such as methanol, ethanol, n-propanol, i-propanol, n-butanol, i-butanol and the isomeric pentanols, hexanols, heptanols and octanols. Those alcohols which form an azeotrope with water and as a result render removal of water by distillation for recycling of the alcohol component impossible, such as, for example, ethanol, n-propanol and isopropanol are particularly preferred. Phenol and substituted phenols, such as cresol or chlorobenzene, which, like the alcohols, are esterifiable organic hydroxy compounds, can furthermore be employed.

Acids to be esterified which may be mentioned for the process according to the invention are, including the carboxyl-C atom: aliphatic saturated or unsaturated, straight-chain or branched $C_1$–$C_{20}$-carboxylic acids, such as formic acid, acetic acid, propionic acid, butyric acid, valeric acid, caproic acid, caprylic acid, capric acid, lauric acid, palmitic acid, stearic acid, acrylic acid, methacrylic acid, crotonic acid, vinyl acetic acid, oleic acid, elaidic acid, linoleic acid, linoleinic acid and anhydrides of these acids; halogen derivatives of such carboxylic acids and their anhydrides; sulfur-containing derivatives of carboxylic acids, such as thiodiglycolic acid; aliphatic saturated or unsaturated $C_2$–$C_{12}$-dicarboxylic acids, such as oxalic acid, malon acid, succinic acid, glutaric acid, adipic acid, suberic acid, maleic acid, fumaric acid and the monomethyl and monohalogen derivatives and anhydrides thereof; cycloaliphatic $C_4$–$C_{12}$-carboxylic acids, such as cyclopropane-carboxylic acid, monomethyl- and dimethyl-cyclopropane carboxylic acid, cyclobutane carboxylic acid, cyclopentane carboxylic acid, cyclohexane carboxylic acid and monomethyl-, dimethyl- and trimethyl-cyclohexane carboxylic acid; aromatic mono- and dicarboxylic acids, such as benzoic acid, phthalic acid, terephthalic acid and nitro-, chloro-, methyl- and hydroxybenzoic acid and anhydrides thereof; and inorganic acids, such as sulfuric acid, phosphoric acid and boric acid.

The joint initial mixture of alcohol, acid and, if appropriate, esterification catalyst in the case of an esterification, or the joint initial mixture of alcohol and alkali metal hydroxide solution in the case of an alcohol formation means that these substances are in the reaction mixture before the start of the boiling operation. However, the lowest-boiling educt is initially present in less than the stoichiometric amount. In general, the lowest-boiling educt is initially introduced to the extent of 10% to below 100% of the stoichiometry, preferably 30% to 80%, at the start of the reaction, the stoichiometry relating to the reactions according to the above formulas (I), (II) or (III).

A completely analogous procedure is possible if, in an esterification reaction between a low-boiling carboxylic acid and an alcohol or phenol having a boiling point above that of the carboxylic acid, the water of reaction is evaporated together with the carboxylic acid and fed along the membrane. In this case, the carboxylic acid is initially introduced in initially less than the stoichiometric amount and is topped up during the reaction.

A procedure which is furthermore completely analogous is possible if a low-water or anhydrous alkali metal alkanolate solution in the alkanol in question is to be prepared from an aqueous alkali metal hydroxide solution and $C_1$–$C_8$-alkanol. Here too, the lower-boiling component of the alkanol (this applies because of the azeotrope formation even for alkanols which boil above 100° C.) is first initially introduced in less than the stoichiometric amount and topped up during the reaction.

The procedure according to the invention does not exclude the reaction component first initially introduced in only less than the stoichiometric amount finally being present in an excess at the end of the reaction and after batchwise or continuous topping up, either because the other particular component is more valuable and is to be reacted completely, or because the component present in excess is to serve as a solvent.

In general, the water of reaction is evaporated off from the reaction mixture together with the lowest-boiling component and is fed along the membrane. In the case of low-boiling esters, this can be this low-boiling ester. In all cases, however, according to the invention the lowest-boiling educt is initially introduced in less than the stoichiometric amount and is topped up only during the reaction.

The membranes used according to the invention can be prepared from, for example, cellulose diacetate, polyimide, cellulose triacetate or polyvinyl alcohol, or can be a pore-free layer prepared by plasma polymerisation. The polymer materials here in general have a molecular weight of between 15,000 and 200,000. Polyvinyl alcohol is in general prepared by substantial hydrolysis of polyvinyl acetate; the degrees of hydrolysis should preferably be more than 95%, particularly preferably more than 98%. Because of the water-solubility of polyvinyl alcohol, this is in general employed in crosslinked form. Such crosslinking can comprise etherification, esterification or acetylization with polyfunctional compounds. Such membranes are known to the expert and are described, for example, in EP-592 883. However, in addition to the organic membranes mentioned, inorganic membranes, such as ceramic membranes or zeolite membranes, can also be employed with the same success.

In the preferred form, composite membranes which in general comprise several layers, that is to say a carrier layer, a porous layer and the actual separating layer, are employed. Possible carrier layers are in general highly porous flexible woven fabrics or nonwovens of fibers, including metal fibers, polyolefins, polysulfones, polyether-imides, polyphenyl sulfides or carbon; porous structures of glass, ceramic, graphite or metals are likewise suitable. The porous supporting layer preferably has an asymmetric pore structure. Such porous supporting layers can be prepared from, for example, polysulfone, polyether-sulfone, polyether-imide, polyvinylidene fluoride, hydrolized cellulose triacetate, polyphenylene sulfide, polyacrilonitrile, polyester, polytetrafluoroethylene, polyethylene, polyvinyl alcohol, copolymers of perfluorinated polyolefins and other suitable polymers. The molecular weights can likewise be in the range from 15,000 to 200,000. The actual separating layer can in turn comprise cellulose diacetate, cellulose triacetate, polyvinyl alcohol or a layer prepared by plasma polymerisation. Polyvinyl alcohol is crosslinked in the manner described above for better resistance to attack by water at higher temperatures. The membranes can be employed as a wound module, plate module, cushion module or hollow fiber or capillary module. Wound modules are particularly preferred.

The temperatures at the membrane chiefly depend, of course, on the stability of the membrane employed. As a rule, the procedure is carried out at temperatures from 50 to 150° C., preferably at 70 to 130° C., particularly preferably at the boiling point of the reaction mixture. The boiling point of the reaction mixture depends on its material composition; the expert is familiar with this. However, these temperatures can be increased or reduced by working under pressure or in vacuo. Increased temperatures and accompanying increases in pressure can prove to be advantageous, for example, if the reaction mixture under normal pressure has a temperature which is below the optimum operating temperature of the membrane used.

A preferred mode of operation is to adjust the boiling point of the reaction mixture, via the content of alcohol at the start and the alcohol topped up in the course of the reaction, such that the temperature of the vapor formed from the reaction mixture does not exceed the maximum permitted operating temperature of the membrane employed, and if appropriate the operating pressure must additionally be adjusted accordingly. Particularly preferably, the temperature of the vapor mixture at which this flows against the membrane module is adjusted such that the maximum operating temperature of the membrane employed is not exceeded. This temperature can differ from that at which the vapor mixture escapes from the reaction mixture.

In a preferred embodiment, the process is carried out by feeding the feed to the membrane module as a mixture of vapor and condensed phase. In this case, some of the vapor is condensed, preferably in a heat exchanger upstream of the module, so that the feed has a content of condensed phase of 5–90% by weight, preferably 5–50% by weight, in particular 10–20% by weight.

A particularly advantageous removal of water from the feed can be achieved if the feed vapor emerging from the membrane module as the retained material is in the saturated vapor state.

The recycling, which preferably proceeds continuously, of the retained material which has been freed from water can be carried out either directly as vapor blown in, or in the form of the condensed phase obtained, if appropriate, by intermediate distillation columns. Recycling in vapor form is preferred.

Both inorganic and organic acids, for example sulfuric acid or p-toluene sulfonic acid, can be used as the acid catalyst to be employed, if appropriate, in the case of an esterification. The possible amounts of the catalyst vary here in the ranges customary for esterification reactions. In many cases, the acid strength of the acid to be esterified is adequate for the catalytic action.

The process can moreover be carried out discontinuously or continuously, it being possible for the continuous procedure to be carried out in a stirred tank with an overflow or, preferably, a reaction column.

In a preferred embodiment, the process according to the invention is carried out by initially introducing the lowest-boiling educt in less than the stoichiometric amount, if appropriate with a catalyst in the case of an esterification, into a reaction tank, adding the acid to be esterified or the alkali metal hydroxide solution and heating the mixture to the boiling point. The vapor mixture formed from the reaction mixture is fed directly or via a distillation column to the membrane in vapor form with contents of condensate formed from the vapor. The water-rich permeate is removed and the retained material is recycled constantly into the reaction mixture during the reaction. In the course of the reaction, the reaction mixture is additionally topped up with the lowest-boiling educt.

When the reaction has ended, in the case of an esterification, the acid constituents of the reaction batch (catalyst, unreacted acid) are neutralized with a base, if appropriate, and the ester is isolated by distillation. Esters are prepared in yields of more than 95% and high purities (greater than 99%) by this process.

In the case of alcoholate formation, a ready-to-use alcoholate solution, which as a rule comprises alcohol as the solvent in an amount beyond the reaction stoichiometry, is present after the water (water of reaction and solution water of the alkali metal hydroxide solution) has been diverted out.

The processes described hitherto in the literature for using vapor permeation/pervaporation for removing water of reaction from the circulation are based on an introduction of the alcohol in more than the stoichiometric amount in the case of an esterification, even if the alcohol is the lowest-boiling educt, in order to achieve an adequate product yield and short reaction times. At least the stoichiometric amount is recommended for optimum operation using vapor permeation/pervaporation. By an initial introduction of less than the stoichiometric amount of the lowest-boiling educt and topping up with the lowest-boiling educt in the course of the reaction, the reaction time is surprisingly reduced significantly in the process according to the invention, for the same degrees of conversion. This applies in a completely analogous manner to the formation of alcoholate. Initial introduction of less than the stoichiometric amount of the lowest-boiling educt in the process described raises the question of reduction in the rate of reaction which, on the basis of initial introduction of less than the stoichiometric amount of the lowest-boiling educt, was to be expected by the expert and should thus lead to an increase in the residence time in the apparatus, which in the end would no longer be acceptable economically. The process according to the invention thus leads, in a manner which is easy to carry out, to a significant reduction in the reaction times required.

The process according to the invention may be demonstrated by the following examples.

EXAMPLES

EXAMPLE 1

152 g of ethanol (about 20% less than stoichiometry) and 5 g of p-toluene sulfonic acid, as the catalyst, were initially introduced into a 2 l stirred tank and the mixture was heated to 50° C. 202 g of maleic anhydride were then added and the mixture was brought to the boiling point under ambient pressure. The vapor mixture formed was fed to a vapor permeation test cell having a membrane area of 0.02 m$^2$ and then recycled into the reaction mixture. The retained material comprised contents of condensate formed from the vapor of about 10% by weight. The membrane used was the type CM-CE-01 from Cm-Celfa. The permeate was condensed under a permeate pressure of 10 mbar and discharged from the vacuum region through a vacuum exchange receiver. In the course of the reaction, the reaction mixture was topped up with further ethanol such that the boiling point was kept constant and the feed temperature to the test cell did not exceed 100° C. The total amount of ethanol topped up was 135 g. A degree of conversion of 98% was achieved over a reaction time of 7 hours.

COMPARISON EXAMPLE 1.1

288 g of ethanol (an excess of about 50%) and 5 g of p-toluene sulfonic acid, as the catalyst, were initially introduced into a 2 l stirred tank and the mixture was heated to 50° C. 202 g of maleic anhydride were then added and the mixture was brought to the boiling point under ambient pressure. The vapor mixture formed was fed to a vapor permeation test cell having a membrane area of 0.02 m$^2$ and the retained material was then recycled into the reaction mixture. The retained material comprised contents of condensate formed from the vapor of about 10% by weight. The membrane employed used was the type CM-CE-01 from Cm-Celfa. The permeate was condensed under a permeate pressure of 10 mbar and discharged from the vacuum region through a vacuum exchange receiver. A degree of conversion of 98% was achieved over a reaction time of 10 hours.

EXAMPLE 2

191 g of ethanol (about 20% less than stoichiometry) and 7 g of p-toluene sulfonic acid, as the catalyst, were initially introduced into a 2 l stirred tank and the mixture was heated to 50° C. 334 g of oxalic acid dihydrate were then added and the mixture was brought to the boiling point under ambient pressure. The vapor mixture formed was fed to a vapor permeation test cell having a membrane area of 0.02 m$^2$ and then recycled into the reaction mixture. The retained material comprised contents of condensate formed from the vapor of about 10% by weight. The membrane employed was the type CM-CE-01 from Cm-Celfa. The permeate was condensed under a permeate pressure of 10 mbar and discharged from the vacuum region through a vacuum exchange receiver. In the course of the reaction, the reaction mixture was topped up with further ethanol, and in particular such that the boiling point was kept constant and the feed temperature to the test cell did not exceed 100° C. The total amount of ethanol topped up was 168 g. A degree of conversion of 98% was achieved over a reaction time of 15 hours.

COMPARISON EXAMPLE 2.1

359 g of ethanol (an excess of about 50%) and 7 g of p-toluene sulfonic acid, as the catalyst, were initially introduced into a 2 l stirred tank and the mixture was heated to 50° C. 334 g of oxalic acid dihydrate were then added and the mixture was brought to the boiling point under ambient pressure. The vapor mixture formed was fed to a vapor permeation test cell having a membrane area of 0.02 m$^2$ and then recycled into the reaction mixture. The retained material comprised contents of condensate formed from the vapor of about 10% by weight. The membrane employed was type CM-CE-01 from Cm-Celfa. The permeate was condensed under a permeate pressure of 10 mbar and discharged from the vacuum region through a vacuum exchange receiver. A degree of conversion of 98% was achieved only after a reaction time of 25 hours.

COMPARISON EXAMPLE 2.2

239 g of ethanol (stoichiometric amount) and 7 g of p-toluene sulfonic acid, as the catalyst, were initially introduced into a 2 l stirred tank and the mixture was heated to 50° C. 334 g of oxalic acid dihydrate were then added and the mixture was brought to the boiling point under ambient pressure. The vapor mixture formed was fed to a vapor permeation test cell having a membrane area of 0.02 m² and then recycled into the reaction mixture. The retained material comprised contents of condensate formed from the vapor of about 10% by weight. The membrane employed was the type CM-CE-01 from Cm-Celfa. The permeate was condensed under a permeate pressure of 10 mbar and discharged from the vacuum region through a vacuum exchange receiver. A degree of conversion of 92% was achieved over a reaction time of 25 hours.

What is claimed is:

1. A process for removing water from a reaction mixture of alcohols and acids or acid anhydrides or a reaction mixture of alcohols and aqueous alkali metal hydroxide solutions, using vapor permeation or pervaporation at the boiling point of the reaction mixture comprising:

(a) initially introducing a first educt and a second educt to form a reaction mixture, the first educt having a lower boiling point than the second educt and the introducing of the first educt involves adding the first educt in less than the stochiometric amount, based on the second educt, wherein the reaction mixture comprises a mixture selected from the group consisting of (i) alcohols and acids (ii) alcohols and acid anhydrides and (iii) alcohols and aqueous alkali metal hydroxide solutions;

(b) heating the reaction mixture to the boiling point of the reaction mixture and feeding vapor mixture formed from the boiling reaction mixture as a feed along a membrane on which water is removed;

(c) recycling the vapor mixture depleted in water into the reaction mixture and topping up the reaction mixture with the first educt during the reaction.

2. The process of claim 1, wherein the alcohols comprise a component selected from the group consisting of $C_1$–$C_8$-alcohols which form an azeotrope with water.

3. The process of claim 1, wherein the membrane has an active layer and the active layer of the membrane used has been prepared from cellulose diacetate, cellulose triacetate, polyvinyl alcohol, polyimide, polyether-sulfone or polyamide or is a pore-free layer prepared by plasma polymerization, a ceramic membrane or a zeolite membrane.

4. The process of claim 1, wherein a composite membrane is employed as the membrane.

5. The process of claim 1, wherein the reaction mixture is heated to the boiling point together with contents of a condensed phase formed from the vapor mixture.

6. The process of claim 5, wherein the content of condensed phase in the feed for the membrane is 5 to 90% by weight.

7. The process of claim 6, wherein the content of condensed phase in the feed for the membrane is 5 to 50% by weight.

8. The process of claim 7, wherein the content of condensed phase in the feed for the membrane is 10 to 20% by weight.

9. The process of claim 1, wherein the first educt is initially introduced together with the second educt in an amount of between 10% to below 100% of the stoichiometric amount.

10. The process of claim 9, wherein the first educt is initially introduced together with the second educt in an amount of between 30% to 80% of the stoichiometric amount.

11. The process of claim 9, wherein the boiling point of the mixture initially introduced does not exceed the maximum permitted operating temperature of the membrane employed.

12. The process of claim 9, wherein the vapor formed from the reaction mixture has a vapor temperature that does not exceed the maximum permitted operating temperature of the membrane employed.

13. The process of claim 12, wherein the vapor mixture flowing to the membrane does not exceed the maximum permitted operating temperature of the membrane employed.

14. The process of claim 9, wherein the mixture is topped up with the first educt such that the maximum permitted operating temperature of the membrane employed is not exceeded during the entire reaction.

15. The process of claim 14, wherein the temperature is kept at the maximum permitted operating temperature of the membrane.

16. The process of claim 1, wherein the process involves an esterification reaction and the process occurs with or without an esterification catalyst.

\* \* \* \* \*